United States Patent [19]

Chatterjee et al.

[11] Patent Number: 5,112,806
[45] Date of Patent: May 12, 1992

[54] ANTIBIOTIC, MERSACIDIN, A PROCESS FOR THE PREPARATION THEREOF AND THE USE THEREOF AS A PHARMACEUTICAL

[75] Inventors: Sukumar Chatterjee; Sugata Chatterjee; Bimal N. Ganguli; Deepak K. Chatterjee; Rajendra K. H. Jani, all of Bombay, India; Richard H. Rupp, Königstein/Taunus, Fed. Rep. of Germany; Hans-Wolfram Fehlhaber, Idstein/Taunus, Fed. Rep. of Germany; Herbert Kogler, Kelkheim, Fed. Rep. of Germany; Gerhard Seibert, Darmstadt, Fed. Rep. of Germany; Volker Teetz, Hofheim am Taunus, Fed. Rep. of Germany

[73] Assignee: Hoechst Aktiengesellschaft, Frankfurt am Main, Fed. Rep. of Germany

[21] Appl. No.: 393,953

[22] Filed: Aug. 15, 1989

[30] Foreign Application Priority Data

Aug. 17, 1988 [DE] Fed. Rep. of Germany ....... 3827868

[51] Int. Cl.$^5$ .................. A61K 37/02; C07K 7/54
[52] U.S. Cl. .......................... 514/9; 514/10; 530/317; 530/323; 435/71.3; 435/252.5; 435/832; 930/190; 930/DIG. 536
[58] Field of Search ............ 530/317, 323; 514/9, 514/10; 435/71.3

[56] References Cited

U.S. PATENT DOCUMENTS 4,493,796  1/1985  Rinehart .................. 530/317

FOREIGN PATENT DOCUMENTS

0192828A3  9/1986  European Pat. Off.

*Primary Examiner*—Christina Chan
*Attorney, Agent, or Firm*—Finnegan, Henderson, Farabow, Garrett and Dunner

[57] ABSTRACT

Mersacidin, a cyclic peptide of the formula I (Abstract continued on next page.)

-continued
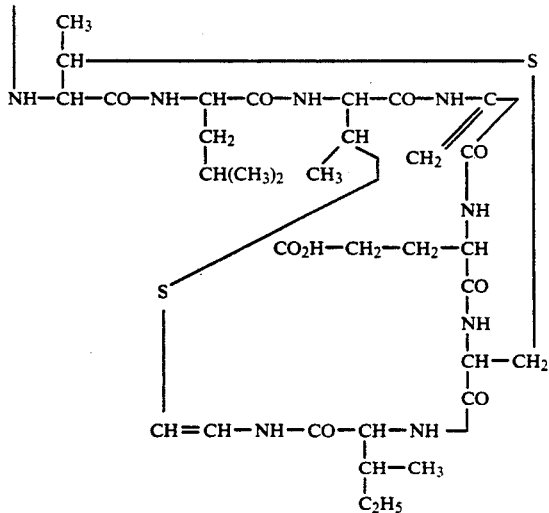
has antibiotic activity.
3 Claims, 3 Drawing Sheets

ANTIBIOTIC, MERSACIDIN, A PROCESS FOR THE PREPARATION THEREOF AND THE USE THEREOF AS A PHARMACEUTICAL

DESCRIPTION

A new antibiotic, mersacidin, a process for the preparation thereof and the use thereof as a pharmaceutical.

The present invention relates to a new antibiotic, which is called mersacidin, to a process for the preparation thereof from the *Eubacterium Bacillus* species Y-85,54728 (deposited on May 10, 1988, in accordance with the provisions of the Budapest Treaty at the Deutsche Sammlung für Mikroorganismen (German Microorganism Collection) under the number DSM 4584), to the variants and mutants thereof and to the use of mersacidin as a pharmaceutical.

The mersacidin according to the invention is a cyclic polypeptide of the formula I

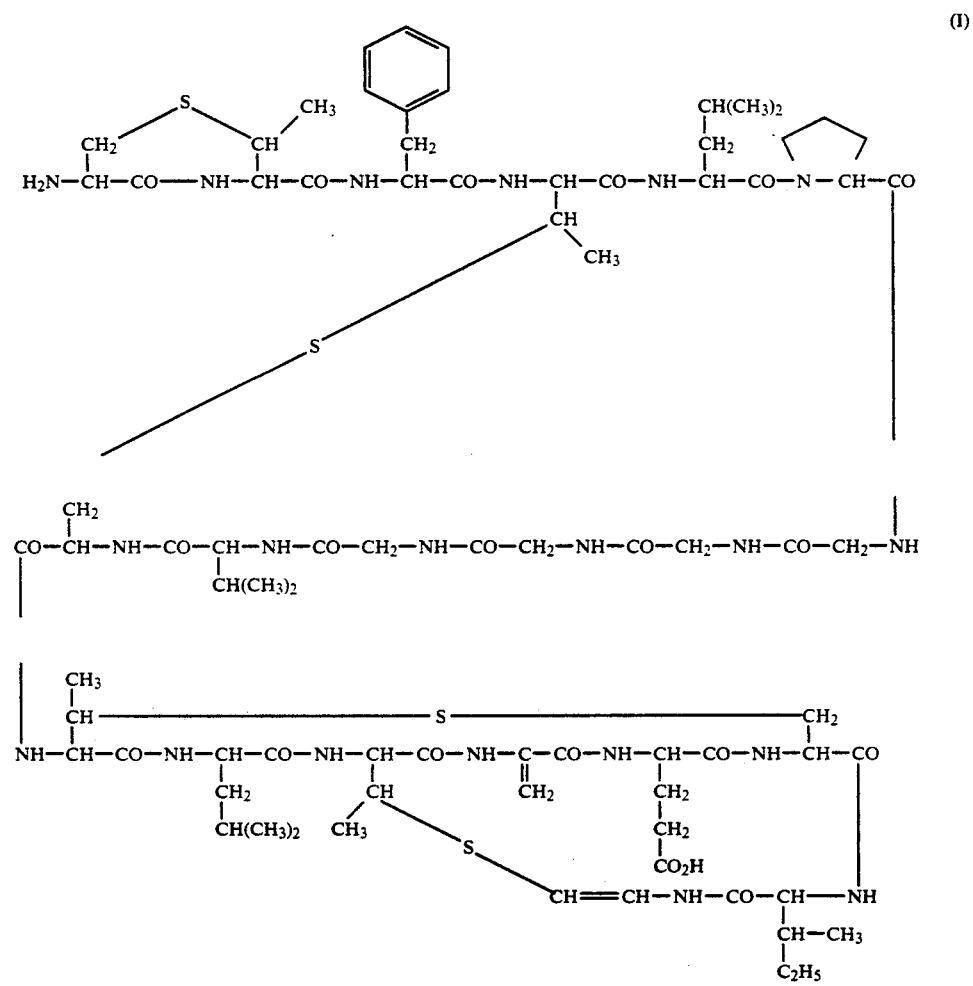

The configuration of the chiral carbon atoms is made clear in formula II.

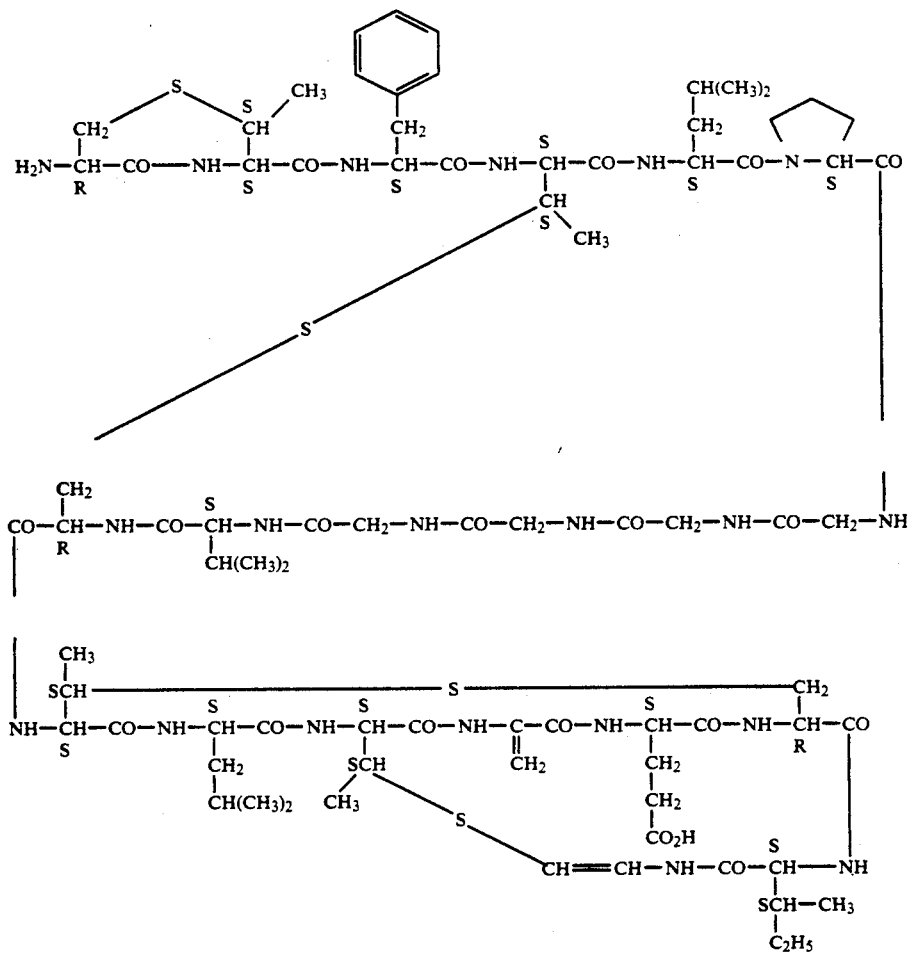

(II)

Figure 1:
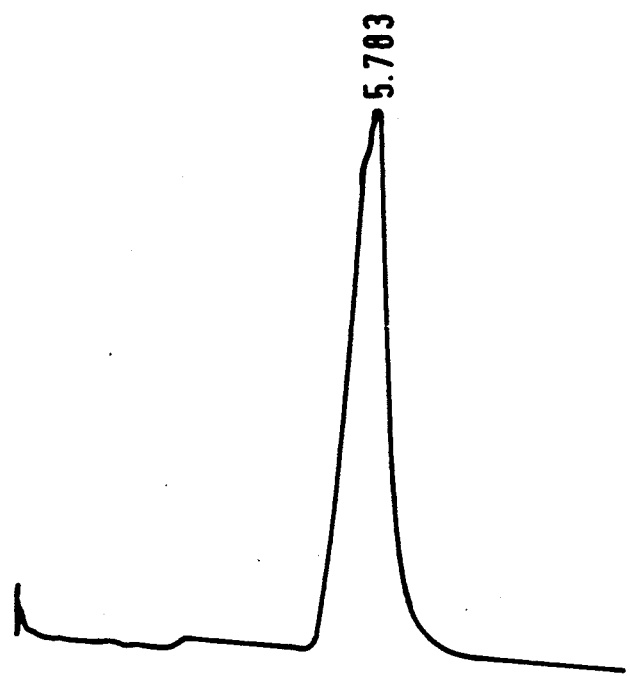
FIG. 1. High-pressure liquid chromatogram of purified mersacidin.

The Eubacterium used for the preparation of mersacidin, Hoechst India Limited culture number Y-85,54728, called Y-85,54728 hereinafter, was isolated from a soil sample obtained in Mulund (saltpan), Maharashtra, India, and identified as a Bacillus species.

Physiologically tolerated salts of mersacidin can be formed in a generally known manner with a wide variety of compounds, for example with organic amines such as, for example, triethylamine or tri-(2-hydroxyethyl)-amine, with alkali metals and alkaline earth metals, such as sodium, potassium, magnesium and calcium, with inorganic acids such as, for example, hydrochloric acid, sulfuric acid or phosphoric acid and with organic acids such as, for example, acetic acid, citric acid, benzoic acid, maleic acid, fumaric acid, tartaric acid or p-toluene-sulfonic acid.

The present invention additionally relates to a process for the preparation of a new antibiotic, mersacidin, from Hoechst India Limited culture number Y-85,54728 as well as the mutants and variants thereof.

The said process comprises the cultivation of culture number Y-85,54728, the mutants and/or variants thereof under aerobic conditions in a nutrient medium containing sources of carbon and of nitrogen, inorganic nutrient salts and trace elements, as well as the isolation and purification of the said antibiotic from the culture broth.

Examples of possible sources of carbon are galactose, glycerol, sucrose or glucose. Galactose is preferred as source of carbon. Preferred sources of nitrogen are yeast extract, beef extract, corn steep liquor, casamino acid or inorganic substances such as, for example, am- The present invention relates not only to mersacidin but also to its physiologically tolerated salts and obvious chemical equivalents.

Cyclic peptide antibiotics are described in the CRC Handbook of antibiotics, volume IV, pages 263–424, "Cyclic Peptides" section. Antibiotics isolated from the genus *Bacillus* are also described in "Antibiotics, origin, nature and properties" edited by Korzybski, T. et al., 1978, volume III, pages 1529–2078. Polypeptide antibiotics from other microbial sources are described in the same publication, volume I, pages 311–491.

However, all the available data indicate that mersacidin differs distinctly from all the cyclic polypeptide antibiotics described in the above publications. No compound which has the molecular weight and the amino acid composition of mersacidin is registered in chemical abstracts.

monium salts. Corn steep liquor is particularly preferred as source of nitrogen. Examples of possible inorganic nutrient salts are sodium hydrogen phosphate, potassium hydrogen phosphate, calcium chloride or magnesium sulfate. Example of possible trace elements are salts of iron, manganese, copper or zinc or other metal salts.

Culture number Y-85,54728 is preferably cultivated at temperatures between 26°–29° C. and pH values between about 6.5 and 7.2. Culture number Y-85,54728 is particularly preferably cultivated at 28° C. ($\pm$ 1° C.) and pH 7.2.

The cultivation is preferably carried out for about 60 to 72 hours, in which case the antibiotic according to the invention is produced in optimal yield. The cultivation is particularly preferably carried out for 66 hours under submerged conditions in shaken flasks as well as in laboratory fermenters. It is possible if required to use a foam suppressant in the fermenters (for example DESMOPHEN ®, polyols from Bayer AG, Leverkusen). The progress of the cultivation and the formation of the mersacidin according to the invention can be established by measuring the bioactivity of the culture broth against *Staphylococcus aureus* 209 P, *Staphylococcus aureus* R 85 and *Alcaligenes faecalis* using the known agar plate diffusion test method (cf., for example, Oxoid Manual 1972, 2nd edition, published by Oxoid Limited, London, England).

The resulting culture broth contains mersacidin only in the culture filtrate which is separated from the mass of cells by centrifugation. Mersacidin can be isolated from the culture filtrate by one or more known processes such as, for example, hydrophobic interaction chromatography, for example on polymeric adsorbents such as DIAION ® HP-20 (Mitsubishi Chemical Industries, Japan) or AMBERLITE ® XAD-2(R), XAD-7(R) adsorbent composed of a matrix of polystyrene, acrylic ester or amine oxide with an average pore diameter of 40–225 × $10^{-10}$m, Rohm & Haas Co., USA), or extraction with solvents which are immiscible with water, such as ethyl acetate or butanol. The preferred process is adsorption on DIAION HP-20 with subsequent desorption of the compound with suitable organic solvents such as, for example, methanol, acetonitrile or aqueous combinations of these solvents. Methanol is preferred as solvent for the elution of mersacidin.

The removal of the solvent from the active eluates yields crude mersacidin. Further purification can be achieved by chromatography on substances such as silica gel, modified silica gel, cellulose or SEPHADEX ® LH-20 (lipophilic gel filtration material manufactured by Pharmacia Fine Chemicals AB, Sweden). Chromatography of crude mersacidin on silica gel using acetonitrile/water mixtures for the elution, by increasing the water concentration stepwise by 5 to 10% each time, represents the preferred process. The active eluates (detected with the biological test method) are concentrated to give the semipure compound. The semipure antibiotic obtained in this way can be further purified, for example, by chromatography on lipophilic gel filtration material such as, for example, SEPHADEX ® LH-20 using solvents such as, for example, water, MeOH, CHCl:, hexane or appropriate combinations thereof, where appropriate with subsequent treatment with activated carbon powder, or by preparative high-pressure liquid chromatography on a silica gel column using solvents such as, for example, MeOH, CH$_3$CN, water or appropriate combinations thereof. Preparative high-pressure liquid chromatography on a column containing HPLC material with octadecyltrichlorosilane groups (such as, for example, the product HYPERSIL ® from Shandon, USA) using a mixture (70:30) of CH$_3$CN and water is the preferred process. Mersacidin is obtained as a white powder after the organic solvent has been removed from the active eluates, for example by distillation in vacuo, and subsequent lyophilization to remove the water.

Mersacidin is qualified by its antibacterial activity (cf. activity test) for use as a pharmaceutical. Accordingly, the invention also relates to pharmaceuticals containing mersacidin in addition to customary, generally known auxiliaries and/or excipients, as well as to the use of mersacidin for the preparation of pharmaceuticals with an antibiotic and/or immunosuppressant action in a manner known per se.

The Examples which follow serve to illustrate the present invention.

EXAMPLE 1

Isolation of culture Y-85,54728 from soil (a) Composition of the nutrient medium for isolation

| Proteose peptone | 20.0 g |
|---|---|
| K$_2$SO$_4$ | 1.5 g |
| MgSO$_4$.7H$_2$O | 1.5 g |
| Glycerol | 10.0 g |
| Agar powder | 15.0 g |
| Demineralized water | 1 liter |
| pH | 6.8 |

(b) Streaking out of soil and isolation 90 ml of sterilized demineralized water were added to 10 g of a soil sample, which had been obtained in a saltpan in Mulund, in a 250 ml Erlenmeyer flask, and the flask was shaken at 220 rpm on an orbital shaker for 2 hours. The above soil suspension was then subjected to serial dilution in steps from 10 to $10^{-5}$. 1 ml of suspension from the final dilution was placed in the centre of a sterile glass Petri plate (6 inches in diameter), and then approximately 50 ml of the above isolation medium, which had been cooled to 45° C., was poured on, and the plate was vigorously shaken. The mixture of soil suspension and medium was left to settle, and it was incubated at 28° C. ($\pm$ 1° C.) for 3 days. The Petri plate was inspected at regular intervals, and culture number Y-85,54728 was isolated from the growing microorganisms.

EXAMPLE 2

Maintenance of the culture Y-85,54728

Composition of the maintenance medium

Culture number Y-85,54728 was maintained on nutrient agar medium of the following composition.

| Peptone | 10 g |
|---|---|
| Beef extract | 3 g |
| Yeast extract | 3 g |
| Agar powder | 15 g |
| Demineralized water | 1 liter |
| pH | 7.2 |

After the ingredients had been completely dissolved by heating they were distributed in test tubes and sterilized at 121° C. for twenty minutes. The test tubes were cooled and left to solidify in a slanting position. Culture number Y-85,54728 was added to the agar slant cultures using a wire loop and they were incubated at 28° C. (± 1° C.) until good growth was visible. The well-grown cultures were stored in a refrigerator at +8° C.

EXAMPLE 3

Fermentation of culture Y-85,54728 in shaken flasks

Composition of the seed culture medium

| Casamino acid | 5 g |
|---|---|
| Corn steep liquor | 5 g |
| Glycerol | 20 g |
| Galactose | 10 g |
| Demineralized water | 1 liter |
| pH | 7.2 |

25 ml portions of the above seed culture medium were distributed over 250 ml Erlenmeyer flasks and heated in an autoclave at 121° C. for 20 minutes. The flasks were cooled, and each was inoculated with one loop of the abovementioned well-grown culture from Example 2 and shaken at 220 revolutions per minute and 28° C. (± 1° C.) for 24 hours. The resulting culture solution was used as seed culture for inoculating the production flasks as described below.

Production of the antibiotic mersacidin in shaken flasks

The production medium corresponded to the seed medium described in Example 3. 100 ml portions of the medium were distributed in 500 ml Erlenmeyer flasks and heated in an autoclave at 121° C. for 20 minutes. The flasks were cooled and then inoculated with the abovementioned seed culture (1% V/V). The fermentation was carried out in an orbital shaker at 220 revolutions per minute and a temperature of 28° C. (± 1° C.) for 66 hours.

The production of the antibiotic was monitored by the profile of bioactivity against *Staphylococcus aureus* 209 P, *Staphylococcus aureus* R 85 and *Alcaligenes faecalis* tested in a known manner using the plate diffusion method. After harvesting, the culture broth was centrifuged, and mersacidin was isolated from the culture filtrate and purified as described below.

EXAMPLE 4

Cultivation of culture number Y-85,54728 in fermenters

Stage 1, Preparation of the seed culture in shaken flasks

The seed culture medium from Example 3 (100 ml) was placed in 500 ml Erlenmeyer flasks with a pH adjusted to 6.8 before sterilization. The latter was sterilized in an autoclave at 121° C. for 20 minutes, cooled and inoculated with one loop of the well-grown culture from Example 2. The flasks were incubated at 28° C. (± 1° C.) in an orbital shaker at 220 revolutions per minute for 24 hours. This grown culture was used to inoculate smaller fermenters as described below.

Stage 2, Preparation of the seed culture in small fermenters 10 liters of the seed medium (as described in Example 3), with a pH adjusted to 6.8 before sterilization, were placed with 0.04% (V/V) DESMOPHEN as foam suppressant in a stainless steel fermenter of capacity 15 liters, sterilized in an autoclave at 121° C. for 36 minutes, cooled and inoculated under aseptic conditions with 4% (V/V) seed material from the above stage 1 of Example 4. Cultivation was then carried out for 24 hours under the following conditions:

| Temperature | 28° C. (±1° C.) |
|---|---|
| Stirring speed | 150 rpm |
| Aeration | 6 liters per minute |

The culture grown after 24 hours was used to inoculate the production medium from stage 3.

Stage 3, Fermentation on the production scale 100 liters of the production medium (corresponding to the seed medium mentioned in Example 3) with the pH adjusted to 6.8 before sterilization and addition of 0.06% DESMOPHEN in a fermenter of capacity 150 liters, or 250 liters of medium with 0.06% DESMOPHEN in a fermenter of capacity 390 liters, were sterilized in situ at 121° C. for 28 minutes and inoculated with 4% of the seed culture from stage 2.

Cultivation was carried out under the following conditions:

| Temperature: | 28° C. (±1° C.) |
|---|---|
| Stirring speed: | 80 to 100 rpm |
| Aeration: | 50 liters per minute (for 100 liter fermenter) |
| | 125 liters per minute (for 390 liter fermenter) |
| Harvesting time: | after 66 hours |

The production of the antibiotic was monitored with the profile of activity tested against *Staphylococcus aureus* 209 P, *Staphylococcus aureus* R 85 and *Alcaligenes faecalis*. After harvesting, the culture broth was centrifuged, and the antibiotic was isolated and purified from the culture filtrate as described below.

EXAMPLE 5

Isolation and purification of mersacidin

About 100 liters of the harvested broth were separated from the mycelium by centrifugation. The resulting filtrate (pH 6.8–7.0) was passed through a 5 liter DIAION HP-20 column. The column was initially washed with 50 liters of demineralized water. It was then washed successively with 70% $H_2O$ in MeOH (40 liters), 50% $H_2O$ in MeOH (50 liters) and 30% $H_2O$ in MeOH (50 liters), and the aqueous washings were all discarded. The column was finally eluted with 10 liters of MeOH. The active eluates were concentrated under reduced pressure to a brown oily substance. The latter was triturated with one liter of petroleum ether (boiling point 40 to 60° C.), filtered and the filtrate was discarded. This procedure was repeated until a powder remained as residue on the filter. Crude mersacidin was obtained as a brownish yellow powder in this way (12 g).

Crude mersacidin was then subjected to medium pressure liquid chromatography on 300 g of silica gel (200 to 300 mesh) in a glass column 5.5 × 53 cm in size. The column was washed with 1.5 liters of $CH_3CN$ and then eluted with 10% aqueous $CH_3CN$ (3 liters) and 15% aqueous $CH_3CN$ (3 liters) at a flow rate of 16 ml per minute. 250 ml fractions were collected and examined by UV detection at a wavelength of 210 nm and by microbial test methods. 6 fractions (1.5 liters) of the 15% strength aqueous $CH_3CN$ eluates were active and were concentrated in vacuo at 35° C. to remove CH₃CN and then freeze-dried, resulting in 2 g of semipure substance as a yellowish powder.

The semipure material obtained in this way was once again subjected to medium pressure liquid chromatography on silica gel (200 to 300 mesh) in a glass column 4 × 54 cm in size. The column was eluted successively with CH₃CN (1 liter), 5% aqueous CH₃CN (1 liter) and 10% aqueous CH₃CN (4.5 liters) at a flow rate of 30 ml per minute. 250 ml fractions were collected and examined by UV detection at 210 nm and by microbial testing. Mersacidin was obtained by elution with 10% strength aqueous CH₃CN (750 ml), which was then concentrated under reduced pressure at 35° C. with subsequent freeze-drying, resulting in 593 mg of mersacidin as a white or whitish powder.

The final purification of mersacidin was carried out by high-pressure liquid chromatography on a HYPERSIL (10 μ) column 4 × 250 mm in size, using 30% strength aqueous CH₃CN as eluent and a flow rate of 1.0 ml per minute. The fractions were examined with a UV detection system at 210 nm. Mersacidin had a retention time of about 3.5 minutes under these conditions. The appropriate fractions were collected, concentrated in vacuo at 35° C. and finally lyophilized, resulting in 275 mg of the antibiotic as a white powder. The purity of mersacidin was examined on an APS-HYPERSIL (5 μ) column 4 × 120 mm in size; mixture (70:30) of CH₃CN and H₂O as eluent; flow rate 1 ml per minute; chart speed 10 mm per minute; detection at 210 nm. The high-pressure liquid chromatogram is shown in FIG. 1.

Physicochemical properties of mersacidin

Mersacidin is a new compound whose structure comprises a nonadecapeptide with a C-terminal vinylamide residue and four intramolecular sulfide bridges.

Table 1 summarizes the physicochemical properties of mersacidin.

TABLE 1

Figure 2:
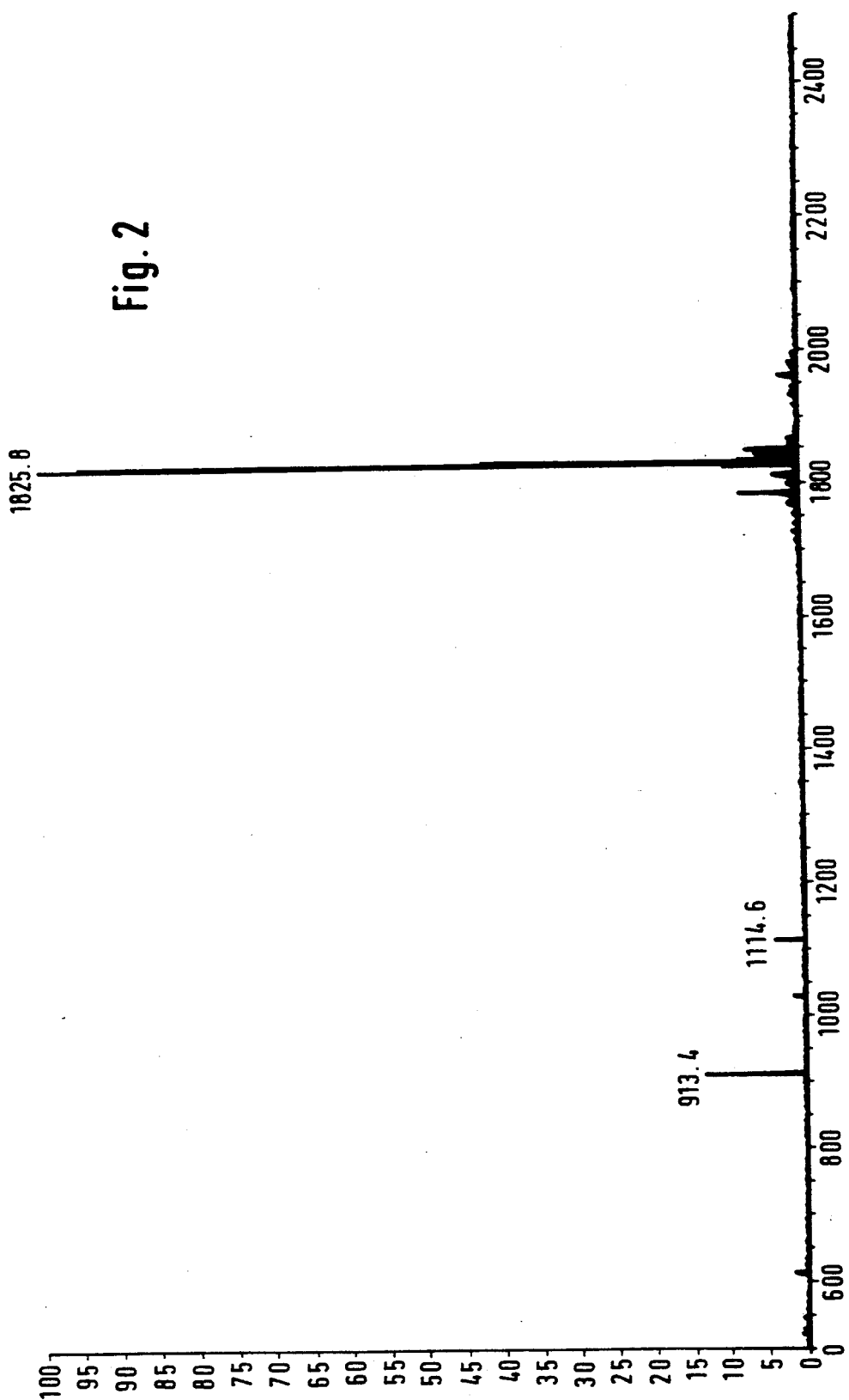
FIG. 2. High-resolution mass spectrogram of mersacidin (FAB ionization, matrix 3-nitrobenzyl alcohol).
Figure 3:
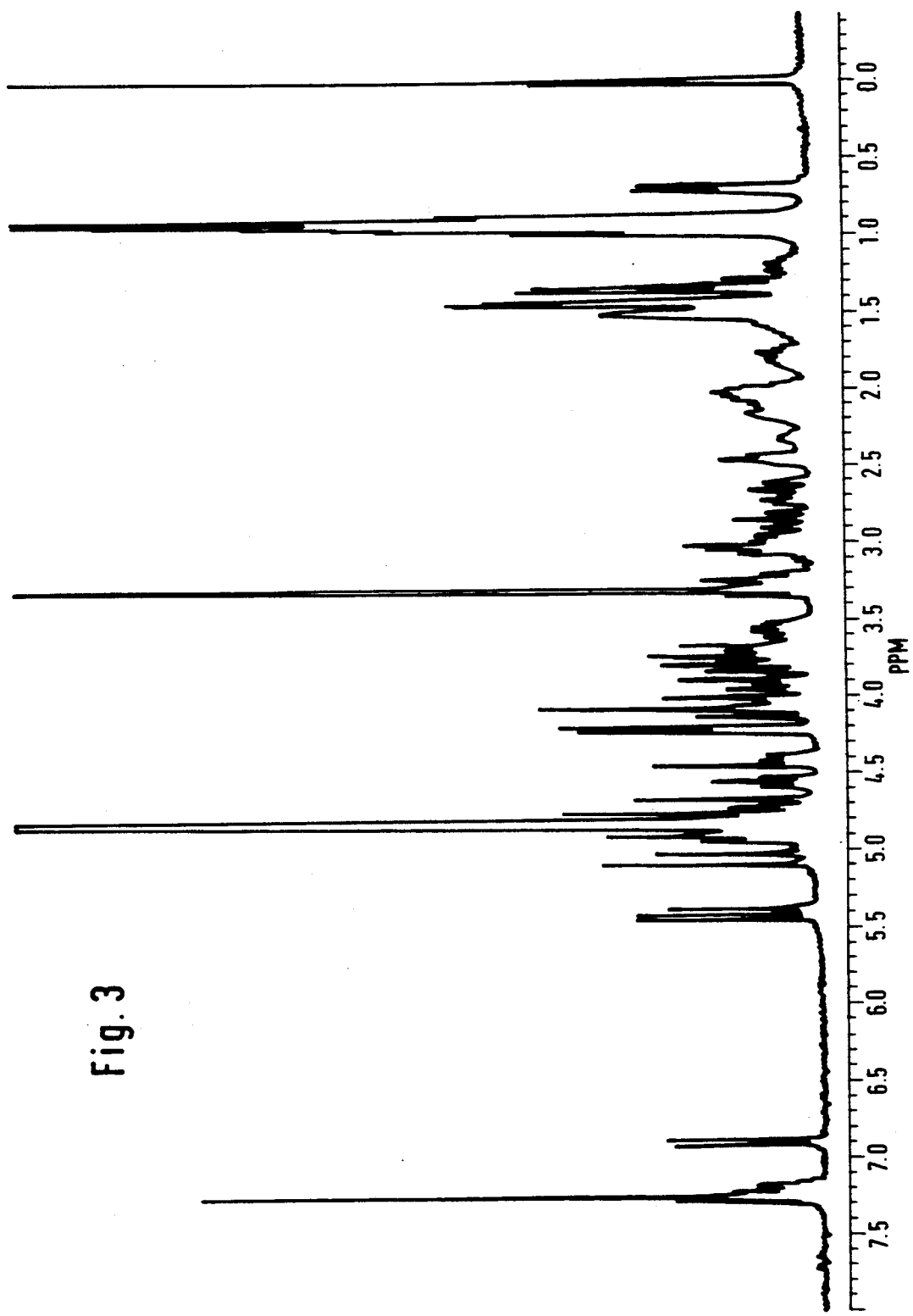
FIG. 3. $^1$H NMR spectrum of mersacidin (270 MHz, CD$_3$OD).

| Physiochemical properties of mersacidin | |
|---|---|
| Appearance: | white amorphous powder |
| Nature: | cyclic polypeptide |
| Melting point: | about 240° C. (decomposition) |
| $[\alpha]_D^{20}$ | −9.4° (c = 0.3, MeOH) |
| Molecular formula: | $C_{80}H_{120}N_{20}O_{21}S_4$ | confirmed by high-resolution mass spectrometry (FAB ionization, matrix 3-nitrobenzyl alcohol)
measured m/z 1825.785 of M+H⁺ion
calculated m/z 1825.790 for $^{12}C_{80}$ $^{1}H_{121}$ $^{14}N_{20}$ $^{16}O_{21}$ $^{32}S_4$ Mass spectrum (FAB, matrix 3-nitrobenzyl alcohol) FIG. 2
¹H NMR spectrum (270 MHz, CD₃OD): FIG. 3
¹³C NMR spectrum (100 MNz, CD₃OD): Tab. 2

TABLE 2

¹³C NMR data of mersacidin
(7% strength solution in CD₃OH. 310K)

| Chemical shift (ppm) | Multiplicity | Structural assignment |
|---|---|---|
| 10.42 | q | C-5 Ile (19) |
| 15.97 | q | C-4' Ile (19) |
| 18.51 | q | C-4 3-thio-Abu (2) |
| 18.68 | q | C-4' Val (11) |
| 19.77 | q | C-4 Val (11) |
| 20.13 | q | C-4 3-thio-Abu (4 + 15) |
| 21.28 | q | C-4 3-thio-Abu (13) |
| 22.43 | t | C-3 Cys (1) |
| 22.43 | q | C-5' Leu (5) |
| 23.17 | q | C-5' Leu (14) |
| 23.53 | q | C-5 Leu (5) |
| 23.58 | q | C-5 Leu (14) |
| 25.47 | d | C-4 Leu (5) |
| 25.78 | d | C-4 Leu (14) |
| 26.00 | t | C-4 Pro (6) |
| 26.68 | t | C-4 Ile (19) |
| 28.17 | t | C-3 Glu (18) |
| 30.85 | t | C-3 Pro (6) |
| 32.54 | d | C-3 Val (11) |
| 33.58 | t | C-3 Cys (12) |
| 35.21 | d | C-3 Ile (19) |
| 35.59 | t | C-4 Glu (17) |
| 37.14 | t | C-3 Cys (18) |
| 37.34 | t | C-3 Phe (3) |
| 39.39 | d | C-3 3-thio-Abu (2) |
| 40.93 | t | C-3 Leu (14) |
| 42.02 | t | C-3 Leu (5) |
| 42.81 | t | C-2 Gly (10) |
| 43.38 | t | C-2 Gly (9) |
| 43.59 | d | C-3 3-thio-Abu (4) |
| 44.10 | t | C-2 Gly (7) |
| 44.62 | t | C-2 Gly (8) |
| 45.50 | d | C-3 3-thio-Abu (13) |
| 48.67 | t | C-5 Pro (6) |
| 49.46 | d | C-3 3-thio-Abu (15) |
| 50.42 | d | C-2 Leu (14) |
| 52.71 | d | C-2 Leu (5) |
| 55.25 | d | C-2 Cys (18) |
| 55.72 | d | C-2 Cys (12) |
| 56.72 | d | C-2 Glu (17) |
| 57.42 | d | C-2 3-thio-Abu (15) |
| 57.81 | d | C-2 Phe (3) |
| 58.12 | d | C-2 Cys (1) |
| 59.07 | d | C-2 3-thio-Abu (2) |
| 59.08 | d | C-2 3-thio-Abu (4) |
| 59.19 | d | C-2 3-thio-Abu (13) |
| 61.60 | d | C-2 Pro (6) |
| 62.64 | d | C-2 Ile (19) |
| 63.14 | d | C-2 Val (11) |
| 103.84 | d | C-2 thiovinylamide (20) |
| 112.41 | t | C-2 dehydro-Ala (16) |
| 127.97 | d | C-7 Phe (3) |
| 129.56 | d | C-1 thiovinylamide (20) |
| 129.71 | d | C-6 Phe (3) |
| 130.22 | d | C-5 Phe (3) |
| 136.96 | s | C-4 Phe (3) |
| 138.15 | s | C-2 dehydro-Ala (16) |
| 166.56 | s | C-1 dehydro-Ala (16) |
| 171.16 | s | C-1 Ile (19) |
| 171.38 | s | C-1 Gly (10) |
| 171.44 | s | C-1 Cys (18) |
| 171.62 | s | C-1 3-thio-Abu (4) |
| 171.76 | s | C-1 3-thio-Abu (15) |
| 171.82 | s | C-1 Gly (9) |
| 171.84 | s | C-1 Leu (5) |
| 171.86 | s | C-1 3-thio-Abu (13) |
| 171.87 | s | C-1 3-thio-Abu (2) |
| 172.59 | s | C-1 Gly (8) |
| 172.74 | s | C-1 Leu (14) |
| 173.06 | s | C-1 Gly (7) |
| 173.76 | s | C-1 Cys (12) |
| 174.00 | s | C-1 Val (11) |
| 174.25 | s | C-1 Glu (17) |
| 174.61 | s | C-1 Cys (1) |
| 174.81 | s | C-1 Phe (3) |
| 175.62 | s | C-1 Pro (6) |
| 181.31 | s | C-5 Glu (17) |

Activity tests a) Activity of mersacidin in vitro

The biological properties of mersacidin as the MIC values required for inhibition of the growth of various microorganisms are listed in Table 3.

TABLE 3

| Number | Test organism | MIC values (μg/ml) |
|---|---|---|
| 1. | Staphylococcus aureus 209P | 0.78–1.56 |
| 2. | S. aureus E 88 | 6.25–12.50 |
| 3. | S. aureus 3066 | 12.50–25.00 |
| 4. | S. aureus 20240 | 3.12–6.25 |
| 5. | S. aureus 20424 | 1.56–3.12 |
| 6. | S. aureus 503 | 0.78–1.56 |
| 7. | S. aureus 789 | 0.78–1.56 |
| 8. | S. aureus 722 | 3.12–6.25 |
| 9. | Staphylococcus aureus SG 511 | 0.39–0.78 |
| 10. | S. aureus 20666 | 3,12–6.25 |
| 11. | S. aureus E 712 | 3,12–6.25 |
| 12. | S. aureus 285 | 0,78–1,56 |
| 13. | S. aureus R 85 | 0,39–0,78 |
| 14. | S. aureus 710 | 0,39–0,78 |
| 15. | Micrococcus luteus | 0,0975–0,195 |
| 16. | Bacillus subtilis | 0,39–0,78 |
| 17. | Streptococcus faecalis | 0,0975–0,195 |
| 18. | Str. D 21777 | 1,56–3,12 |
| 19. | S. epidermidis MRSE | 0,5–16,0 |
| 20. | S. epidermidis MSSE | 0,5–16,0 |
| 21. | Group A Streptococci | 0,5–8,0 |
| 22. | Group B Streptococci | 1,0–8,0 |
| 23. | Group C Streptococci | 2,0–64 |
| 24. | Group G Streptococci | 2,0–8,0 |
| 25. | Streptococcus bovis | 4,0–32,0 |
| 26. | Streptococcus viridans | 0,5–32,0 |
| 27. | Streptococcus faecalis | 64,0 |
| 28. | Streptococcus pneumoniae | 1,0–4,0 |
| 29. | Cornybacterium JK | 2,0–4,0 |
| 30. | Listeria monocyctogenes | 16,0–64,0 |
| 31. | Clostridium species | 0,5–16,0 |
| 32. | Peptostreptococci species | 0,5–8,0 |
| 33. | Propionibacterium genes | 1,0–16,0 | b) Activity of mersacidin in vivo

Mersacidin showed good activity in the in vivo system of laboratory mice. On subcutaneous administration in a dose of 9.37 and 25.00 mg/kg to laboratory mice infected experimentally with Staphylococcus aureus SG 511 and S. aureus 710 (resistant to methicillin), laboratory mice. Even at a dose of 500 mg/kg (subcutaneous), the highest concentration tested to date, no animal mortality was observed. The results are listed in Table 4.

TABLE 4

In vivo activity of mersacidin against S. aureus SG 511 infection in mice compared with vancomycin.
Inoculation medium used: 1.75 × 10$^9$ CFU/mouse

| Compound | Dose/administration mg/kg × 3, s.c. | Number of mice treated/cured (percentage rate of cure) | Approx. ED$_{50}$, ED$_{90}$ mg/kg × 3 |
|---|---|---|---|
| Mersacidin | 9.37 | 53/53 (100) | |
| | 6.25 | 38/40 (95) | 2.59 |
| | 3.12 | 18/27 (67) | 5.38 |
| | 1.60 | 3/24 (12) | |
| | 0.80 | 0/27 (0) | |
| Vancomycin | 18.75 | 71/71 (100) | |
| | 12.5 | 59/61 (97) | 7.20 |
| | 9.37 | 48/53 (85) | 9.37 |
| | 6.25 | 13/44 (29) | |
| | 3.12 | 2/41 (5) | |

In vivo activity of mersacidin against S. aureus E 710 (MRSA) in mice, in comparison with vancomycin Inoculation medium used: 5 × 10$^9$ CFU/mouse (1 MLD)

| Compound | Dose/administration mg/kg × 3. s.c. | Number of mice treated/cured (percentage rate of cure) | Approx. ED$_{50}$, ED$_{90}$ mg/kg × 3 |
|---|---|---|---|
| Mersacidin | 25.00 | 12/12 (100) | 10.81 |
| | 12.50 | 10/16 (63) | 19.59 |
| | 9.37 | 4/10 (40) | |
| | 6.25 | 1/10 (10) | |
| Vancomycin | 37.00 | 6/6 (100) | 18.94 |
| | 25.00 | 14/21 (67) | 32.01 |
| | 12.50 | 3/11 (27) | |
| | 6.25 | 0/11 (0) | |

In vivo activity of mersacidin against S. aureus SG 511 abscess in rats, compared with vancomycin.

Infecting dose : 2 × 10$^{-9}$ CFU in 5% mucin, injected under the skin.
Treatment: 50 mg/kg × 7 days
Results: Mersacidin reduces bacterial counts by 1.4 log$_{10}$ CFU/ml (colony forming units)
Vancomycin reduces bacterial counts by 0.79 log$_{10}$ CFU/ml (colony forming units).

EXAMPLE 6

The preparation of soluble salts of mersacidin

Mersacidin can be made water soluble in the form of its alkali metal salts. These salts can be prepared by the treatment of mersacidin with 1.0 equivalent of the corresponding alkali metal hydroxide in the presence of pyridine. For example, mersacidin (50 mg) was dissolved in 1 ml of pyridine, the solution cooled to 0° C. and a solution of 1.683 mg of KOH in 3 ml of distilled water was added under stirring. The mixture was stirred at 0° C. for 1 h and then lyophilized to give 49 mg of potassium mersacidin as a white powder. This potassium mersacidin was freely soluble up to 160 mg/ml of water. The in vitro and in vivo antibactericidal properties of potassium mersacidin are comparable to those of mersacidin and are given in Tables 5 and 6.

TABLE 5

MIC of potassium mersacidin

| No. | Test Organism | MIC values (μg/ml) |
|---|---|---|
| 1. | Staphylococcus aureus 209P | 2 |
| 2. | S. aureus R 85 | 2 |
| 3. | S. aureus 710 | 1 |
| 4. | S. aureus 3066 | 10 |
| 5. | S. aureus 25923 | 8 |
| 6. | S. epidermidis 32965 | 6 |
| 7. | S. epidermidis 823 | 50 |
| 8. | S. haemolyticus 712 | 10 |
| 9. | S. haemolyticus 809 | 4 |
| 10. | Streptococcus hominis ML 22 | 10 |
| 11. | Streptococcus faecalis 29212 | 15 |
| 12. | Streptococcus faecalis 21777 | 15 |

TABLE 6

In vivo activity of potassium mersacidin against S. aureus and Streptococcus pyogenes A 77 infection in mice

| Strain | Inculum CFU/mouse | 50% Effective Dose (ED$_{50}$) mg/kg × 3, s.c. |
|---|---|---|
| S. aureus SG 511 (Methicillin sensitive) | 1,75 × 10$^9$ | 2,85 |
| S. aureus E 710 (Methicillin resistant) | 1 × 10$^{10}$ | 6,72 |
| S. aureus C 31153 (Methicillin & Caphalexin resistant) | 2 × 10$^9$ | 15,35 |
| Streptococcus pyogenes | 3,8 × 10$^3$ | 0,46 |

| TABLE 6-continued | | |
|---|---|---|
| In vivo activity of potassium mersacidin against *S. aureus* and *Streptococcus pyogenes* A 77 infection in mice | | |
| Strain | Inculum CFU/mouse | 50% Effective Dose (ED$_{50}$) mg/kg × 3, s.c. |
| A 77 | | |

We claim:
1. A compound of the formula I

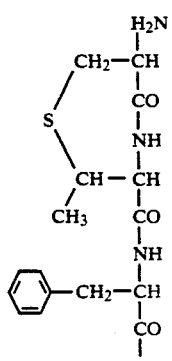
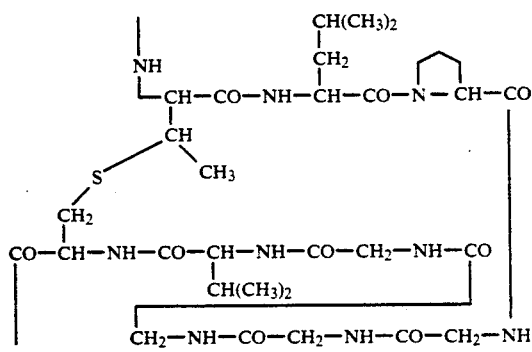

(I)

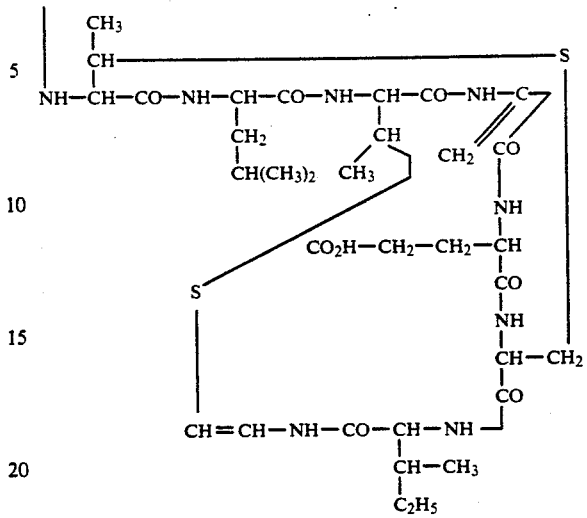

as made by and isolated from the cultivation of *Eubacterium Bacillus* sp. Y-85,54728 (DSM 4584), or a physiologically tolerated salt thereof.

2. A compound of the formula II

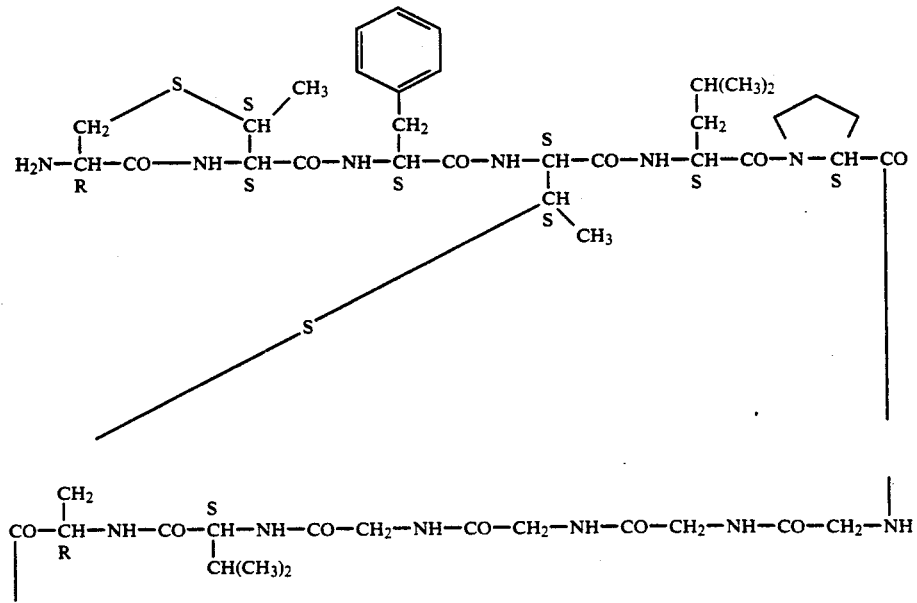

(II)

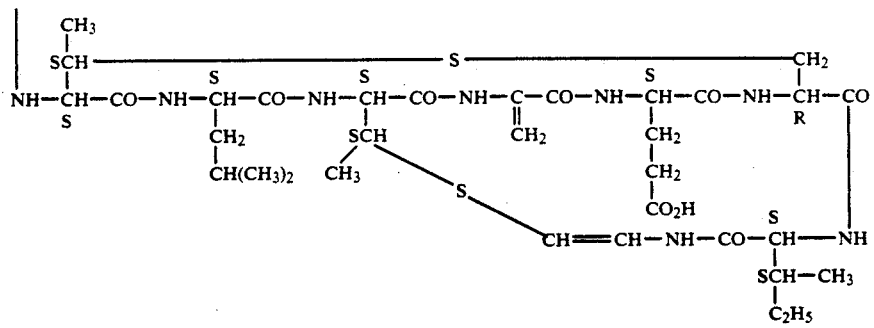
or a physiologically tolerated salt thereof.
3. A pharmaceutical composition comprising an antibiotically effective amount of a compound as claimed in claim 1, and a pharmacologically acceptable carrier.
* * * * *